US007330243B2

(12) United States Patent
Betzel et al.

(10) Patent No.: US 7,330,243 B2
(45) Date of Patent: Feb. 12, 2008

(54) METHOD FOR MONITORING THE PRODUCTION OF BIOMOLECULE CRYSTALS

(75) Inventors: Christian Betzel, Hamburg (DE); Karsten Dierks, Hamburg (DE); Gert Rapp, Hamburg (DE)

(73) Assignees: Rina-Netzwerk RNA Technologien GmbH, Berlin (DE); Rapp OptoElectronic GmbH, Hamburg (DE)

( * ) Notice: Subject to any disclaimer, the term of this patent is extended or adjusted under 35 U.S.C. 154(b) by 441 days.

(21) Appl. No.: 11/052,324

(22) Filed: Feb. 7, 2005

(65) Prior Publication Data

US 2005/0172887 A1 Aug. 11, 2005

(30) Foreign Application Priority Data

Feb. 5, 2004 (DE) ..................... 10 2004 005 878

(51) Int. Cl.
*G01N 21/64* (2006.01)
*G01N 15/02* (2006.01)
*G01N 21/49* (2006.01)

(52) U.S. Cl. .......................... 356/72; 356/73; 356/336; 356/318; 356/417

(58) Field of Classification Search .................. 356/72, 356/73, 336

See application file for complete search history.

(56) References Cited

U.S. PATENT DOCUMENTS

2004/0007672 A1* 1/2004 DeLucas et al. ............ 250/373
2006/0111555 A1* 5/2006 Hoffmann .................. 530/350

FOREIGN PATENT DOCUMENTS

| | | | |
|---|---|---|---|
| EP | 1 022 549 | A1 | 7/2000 |
| WO | WO 02/081502 | A2 | 10/2002 |
| WO | WO 2004/012841 | A1 * | 2/2004 |

* cited by examiner

*Primary Examiner*—F. L. Evans
(74) *Attorney, Agent, or Firm*—Mayer & Williams PC; Keum J. Park, Esq.

(57) ABSTRACT

The invention relates to a method for monitoring the production of macromolecule crystals containing at least one fluorescence emitter, comprising the following steps: a) a solution volume with dissolved macromolecules of a molecule species containing at least one fluorescence emitter is subjected to conditions, which cause the macromolecules to crystallize to macromolecule crystals or which are expected to cause the macromolecules to crystallize to macromolecule crystals, b) the solution volume of step a is irradiated with coherent light, and the light scattered by the macromolecule crystals is detected in at least one defined spatial angle range by means for the detection scattered light, c) before, simultaneously with or after step b, the solution volume is irradiated with a light source, the light emission of which is suitable for exciting the fluorescence emitter, and the fluorescence light is detected by means for the detection of fluorescence light, and to a device for carrying-out the method.

20 Claims, 1 Drawing Sheet

METHOD FOR MONITORING THE PRODUCTION OF BIOMOLECULE CRYSTALS

FIELD OF THE INVENTION

Figure 1:
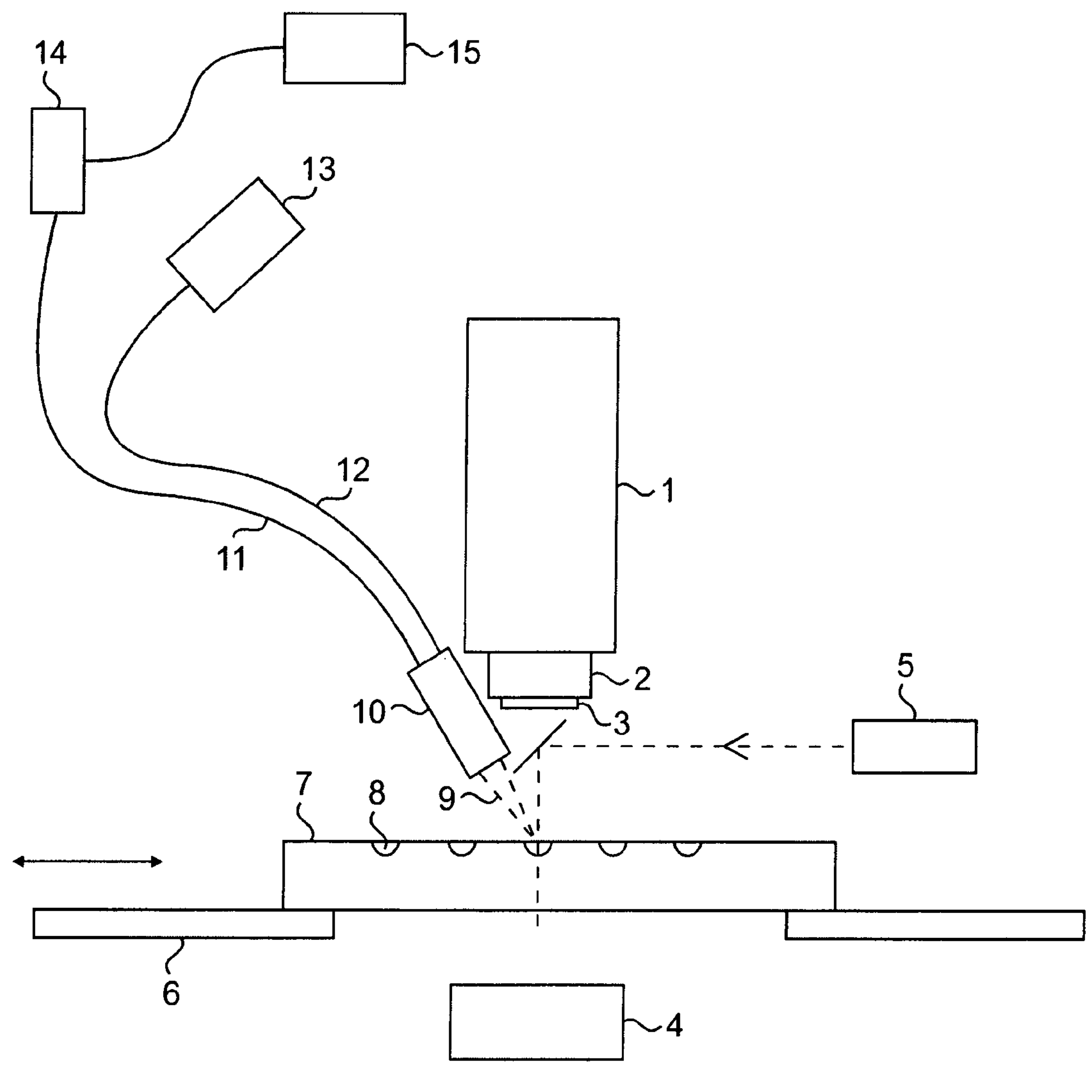

The invention relates to a method for monitoring the production of biomolecule crystals containing at least one fluorescence emitter, comprising the following steps: a solution volume with dissolved biomolecules containing at least one fluorescence emitter is subjected to conditions, which cause the biomolecules to crystallize to biomolecule crystals or which are expected to cause the biomolecules to crystallize to biomolecule crystals; the solution volume is irradiated with a light source, the light emission of which is suitable for the excitation of the fluorescence emitter, and fluorescence light is detected by means for the detection of fluorescence light; and the signals generated by the means for the detection of fluorescence light are fed to an evaluation unit, in which the signals are transformed into a fluorescence intensity, and the fluorescence intensity is compared to a required fluorescence intensity.

BACKGROUND OF THE INVENTION AND PRIOR ART

From the document EP 1 022 549 A1 is known in the art a method, wherein a liquid containing microparticles or nanoparticles is irradiated with light being coherent in time and space, for instance generated with a laser, at a multitude of discrete wavelengths, wherein back-scattered radiation is detected, and wherein intensity fluctuations of the scattered radiation at each of the irradiated wavelengths are determined. This is a variant of the dynamic Light Scattering (DLS) or Photon Correlation Spectroscopy (PCS) method, where by using different wavelengths, measurements with different scattering angles for the purpose of the compensation for multiple-scattering effects, inter alia, are not needed. By this method, by measurement of the time dependences of the fluctuations and autocorrelation of the resulting function, a determination of the particle size distribution or of particle sizes can be performed. Further, in this document, devices for carrying-out the method are described in detail. These devices basically comprise a defined number (2 or more) of lasers with different emission wavelengths (in the visible light up to the near IR), the light of which is conducted to the sample by, for instance, optical conductors. Back-scattered light is simultaneously collected by means of optical conductors, detected and evaluated.

From the document WO 02/081502 A2 is known in the art a method for optimizing crystallization tests in the context of high-throughput crystallization tests, wherein a solution of a gel-forming component containing biomolecules of a biomolecule species is reacted with another substance promoting the crystallization by means of an automatic device for delivery of the substance. Thereby, a multitude of solutions that are disposed for instance as a multitude of drops on a plate, can be subjected with high throughput to crystallization tests.

For crystallization tests on biomolecules, for instance in order to produce crystals for the purpose of the x-ray structure analysis, it is necessary to check the crystallization process, and in addition, biomolecule crystals have to be distinguished from salt crystals that may also be possibly generated. In practice, this takes place, for instance, by observing the solution containing a biomolecule species by means of simple optical methods, for instance by using a microscope. With respect to the regularly existing difficulty to crystallize biomolecules or to provide suitable crystallization conditions, often a multitude of crystallization tests are required. The prior crystallization methods, also the above high-throughput methods, include as a substantial time-critical step the detection of successful crystallization, since the observation by an operator is expensive and further comes along with a relatively high fault probability.

TECHNICAL OBJECT OF THE INVENTION

It is therefore the technical object of the invention to provide a method and a device, by means of which the generation of biomolecule crystals can easily, quickly, reliably and in particular automatically be detected.

BASICS OF THE INVENTION AND EMBODIMENTS THEREOF

For achieving this technical object, the invention teaches a method for monitoring the production of macromolecule crystals, comprising the following steps: a) a solution volume with dissolved macromolecules containing at least one fluorescence emitter is subjected to conditions, which cause the macromolecules to crystallize to macromolecule crystals or which are expected to cause the macromolecules to crystallize to macromolecule crystals, b) the solution volume of step a is irradiated with coherent light, and the light scattered by the macromolecule crystals is detected in at least one defined spatial angle range by means for the detection of scattered light, c) before, simultaneously with or after step b, the solution volume is irradiated with a light source, the light emission of which is suitable for exciting the fluorescence emitter, and fluorescence light is detected by means for the detection of fluorescence light.

The detection of fluorescence light may take place in particular as a two-dimensional fluorescence photograph of the solution volume.

The method according to the invention is in particular suitable for biomolecules. Therefore, the following explanations relate to biomolecule crystals; they are, however, also applicable to any macromolecule.

The invention basically combines two different per se known methods for the automated monitoring of the generation of biomolecule crystals. The measurement of (back-) scattered coherent light serves at last for the detection, whether at all crystals are generated, and if yes, of the size of such crystals, and the measurement of the fluorescence light or the taking of the fluorescence photograph serves for distinguishing biomolecule crystals from for instance salt crystals, which typically do not contain a fluorescence emitter. By this combination, the generation of biomolecule crystals is detected with a high safety level, also discriminating any salt crystal formation. If in step b), above, a particle generation is detected, and the fluorescence photograph does not show any dot areas of high fluorescence intensity, then the particles are salt crystals. If however in step b) dot areas of high fluorescence intensity are simultaneously measured, then the dot areas are macromolecule crystals.

An automation of the method according to the invention is readily made possible by adding the following steps: d) the signals produced by the means for the detection of scattered light are fed to an evaluation unit, in which the signals are transformed into a particle size or a measurement value correlated herewith, the particle size or the measurement value being compared to a defined required particle size or required measurement value, e) the signals produced by the means for the detection of fluorescence light are fed to an evaluation unit, in which the signals are transformed into a fluorescence intensity, and the fluorescence intensity (resolved in an image plane or of the dot areas of maximum fluorescence intensity in a fluorescence photograph) is compared to a required fluorescence intensity, f) biocrystals are selected, if the particle size is larger than the required particle size or the measurement value is larger than the required measurement value and simultaneously the fluorescence intensity is larger than the required the fluorescence intensity.

By comparing the particle size to the required particle size or of the measurement value to the required measurement value, and of the fluorescence intensity to the required fluorescence intensity, an automatic detection takes place, if i) crystals are generated, and ii) the generated crystals are biocrystals. The required particle size can be taken as a very small value, and then the crystal generation per se is detected. The value may, however, be selected such that the crystal size is for instance sufficient for x-ray structure analyses. In the case of the required fluorescence intensity, the value thereof is at least the factor 2 of the fluorescence radiation emitted by the same solution. However, the biomolecules are completely in solution, under otherwise identical conditions (a crystal has a higher fluorescence intensity than the solution because of the spatial concentration of the molecules in the crystal). In any case, when both criteria are fulfilled, a signal is produced, which indicates the positive biocrystallization test. Such signals can then be used for controlling further processes and/or automatic handling devices.

In principle, the method according to the invention can already be used, also in the automated version, when monitoring a single crystallization test. It is particularly effective and consequently has quick results with regard to a successful production of a biocrystal, if a multitude of solution volumes comprising identical or different biomolecules are subjected simultaneously or subsequently to the steps a) to f), and the crystallization conditions of step a) can be identical or different in the various solution volumes, and the multitude of solution volumes are preferably arranged on or in a carrier element.

Suitable carrier elements are for instance so-called multiwell plates having a multitude, for instance 96, depressions, where solutions can be accommodated. Such plates are standardized, and a multitude of automated devices are available for automatically filling and automatically handling such plates. In another variant, the carrier element does not have any depressions, but its plane surface is hydrophobic, except for closed sample areas. Such plates are known in the art, as are suitable hydrophobation coatings. With these plates, a solution is applied as drops in a sample area, and due to the surrounding hydrophobic surface, a spreading of the drop and thus the risk of mixing with adjacent drops is prevented.

The number of solution volumes or depressions or sample areas may in principle be in the range 5 to 1,000, preferably 50 to 500.

In principle, the sequence of steps b) and c) is arbitrary, and may also, for instance, occur simultaneously. A high throughput with at the same time high miniaturization of a device according to the invention is then achievable, if steps b) and c) are performed one after the other, b) after c) or c) after b). Then, for instance, light conductors directed onto a solution volume can be used for both steps, and separate light conductors need not be provided for the steps.

The step b) can be executed in different variants. In the case of a few generated crystals only, it may be sufficient to use coherent light of one wavelength only and to perform the detection of the scattered light at one back-scattering angle only. If only very few crystals exist, on the one hand the probabilities of multiple scattering are reduced, and on the other hand, because of the low number of crystals per volume unit, less falsifications by reduced average free path lengths of the crystals subjected to Brownian movements take place. Any falsifications of results, in particular with a high number of crystals per volume unit, can be prevented, if coherent light is irradiated at different discrete wavelengths, and the intensity fluctuations of the (back-)scattered light are measured for selected wavelengths. The measurements at different wavelengths can be made simultaneously or subsequently. With simultaneous measurement, in principle, as with subsequent measurement, the irradiation of the primary light and detection of the scattered light can be performed by means of one single light conductor. This requires, on the detector side, a suitable resolution according to wavelengths. It is, however, also possible to work with one primary light conductor for each wavelength and/or with one scattered light conductor for each wavelength, thus the expenses on the detector side is reduced to filtering only the desired wavelength. In principle, it is also possible to perform, for instance by means of Fourier transformation algorithms, the evaluation of intensity fluctuations at different wavelengths, thus possibly obviating the need for expensive filter apparatuses or spectroscopes.

Alternatively, of course, for compensating the falsifications by multiple scattering and high particle densities, the detection of the scattered light in different defined backscattering angles with irradiation of one single wavelength can be used, what possibly might be preferred.

For generating the coherent light of step b), preferably lasers can be used. The emission wavelengths may be in the visible light and IR, for instance near IR range. The light source used in step c) may, for instance, be a UV light source being usual for fluorescence excitation; however, light sources in the visible range are in principle not excluded. The wavelength of the fluorescence light to be detected may be in the UV range, or also in the visible range.

The light source used in step c) may emit polarized light. In this case, the fluorescence light in turn is also polarized. Then for the detection of the fluorescence light, a polarization filter may be provided, which permits a discrimination of foreign light as well as of scattered light.

In principle, the coherent light of step b) and/or the light of the light source of step c) may be directed by any usual optical means onto the solution volume and if applicable focused thereinto. Corresponding considerations apply for the reception of the scattered light and/or of the fluorescence light. Foreign light influences may however particularly effectively be prevented, if the sources for coherent light and/or for fluorescence excitation and/or the means for the detection of scattered light and/or the means for the detection of fluorescence light comprise a light conductor connected thereto with one of its ends, and the opposite end of which is directed onto the solution volume. The ends directed onto the solution volume may then be positioned very closely to the solution volume. Further, the ends may so to speak be bundled, so that a very compact measuring head is generated, which permits use even for very small and tightly arranged solution volumes, as required for high-throughput experiments.

For the means for the detection of the fluorescence light, suitable optical elements may be used such that the solution volume or at least a part thereof is imaged as a fluorescence photograph onto a detector operating with a two-dimensional spatial resolution, for instance a CCD being sensitive in the range of the fluorescence light wavelength.

The means for the detection of the scattered light and/or of the fluorescence light may in principle be arbitrary. These may for instance be semiconductor detectors, which may operate, for example, in an inherently wavelength-selective manner. High sensitivities are however obtained, if the said means comprises a classic photomultiplier. In step c), a UV filter may be interposed between the solution volume and the means for the detection of fluorescence light, for instance between a light conductor and the means connected thereto for the detection of fluorescence light or in front of the lens of a camera.

The invention further teaches a device for monitoring, preferably high-throughput monitoring, the production of biocrystals, comprising a carrier element disposed on a base element, and onto or into said carrier element a solution volume containing dissolved biomolecules can be applied, a light source for coherent light to be directed onto the solution volume, a light source for light, which is suitable for the excitation of a fluorescence emitter, to be directed onto the solution volume, means for the detection of scattered light from the solution volume, means for the detection of fluorescence light from the solution volume, and an evaluation unit connected to the means for the detection of scattered light and the means for the detection of fluorescence light. In principle, the above explanations of the method according to the invention also apply in an analogous manner to the device according to the invention, too.

For the purpose of carrying-out high-throughput crystallization experiments it is recommended that the carrier element comprises a multitude of sample areas for receiving one solution volume each. The light source for generating coherent light and/or the light source for generating light suitable for the excitation of the fluorescence emitter and/or the means for the detection of scattered light and/or the means for the detection of fluorescence light may either comprise a common light conductor or one assigned light conductor each, the free end of which is directed onto the solution volume. It is also possible that for instance one light conductor is assigned to a partial amount of the light sources and one light conductor is assigned to the means for the detection. Any combinations of multiple use of light conductors are possible.

The free end of the light conductor may be provided for receiving light, which is emitted from the solution volume in an angle of 0° to 170°, for instance 0° to 80°, with respect to the axis of the irradiated light.

For the purpose of a fully automatic monitoring, the carrier element or the light sources, the means for the detection of scattered light and the means for the detection of fluorescence light may be displaceable relative to the base element by means of a manipulator device. This will in particular be recommendable for carrier elements, which carry a multitude of solution volumes, since then the solution volumes can successively be subjected to the method according to the invention by moving the solution volume to a measurement position, and that automatically controlled. Herein, the manipulator control is achieved by a step-on signal generated by the evaluation unit, which signals the termination of the execution of the method according to the invention for a solution volume and generates control signals in the manipulator control for causing a relative movement of solution volumes and the other components mentioned above, such that the investigated solution volume is removed from the measurement position and is replaced by another solution volume still to be investigated.

Of its own importance and fully independent from the above method is a method according to the invention for centering a macromolecule crystal of macromolecules from a macromolecule species containing a fluorescence emitter in an apparatus, for instance an x-ray diffraction apparatus, wherein a crystal holder with the macromolecule crystal is irradiated with light suitable for the fluorescence excitation of the fluorescence emitter, wherein a fluorescence photograph of the area of the crystal holder is recorded, wherein spatial coordinates of the recorded fluorescence photograph are correlated with spatial coordinates of a required crystal position in the apparatus, and wherein the spatial coordinates of a fluorescence image of the macromolecule crystal in the fluorescence photograph are compared to the spatial coordinates of the required crystal position. In the case that in the above comparison a defined maximum difference is exceeded, a correction of the position of the crystal holder can be made manually or automatically. The latter permits the execution of the high-throughput x-ray structure analysis, because of the automation. Suitable positioning technologies including the respective manipulators are known to the man skilled in the art. This aspect of the invention is based on that a fluorescent macromolecule crystal fluoresces because of the concentration of the fluorescence emitters with a very high intensity, compared to the surrounding solution and/or the crystal holder (for instance a loop of an organic polymeric material, such as Rayon). Because of the high contrast, thus, a safe identification of the macromolecule crystal and its spatial arrangement in the crystal holder is possible, with imaging methods, and is used for the exact positioning in the x-ray diffraction apparatus.

Definitions

Biomolecule crystals are crystals, the crystallographic repetition units of which are formed by biomolecules. Biomolecule crystals generate defined x-ray diffraction patterns, from which the spatial arrangement of the atoms of the biomolecule can be determined.

Biomolecules are typically macromolecular organic compounds, which exist in natural organisms or which themselves do not exist in natural organisms, but which are formed are formed from naturally existing molecular components, or which are formed from molecular components, which are modified with respect to natural molecular components. The latter components are for instance components, which are modified by incorporation of a fluorescence emitter. Examples of such components are: natural amino acids, non-natural isoforms of natural amino acids, chemically modified amino acids, natural nucleotides, chemically modified nucleotides, sugar and lipids. Examples biomolecules are peptides, proteins, antibodies, receptors, enzymes, of steroids, oligonucleotides, polynucleotides, ribozymes, aptamers, complexes of several different or identical molecules of the above type, but also complex structures, such as cell nuclei and viruses.

Macromolecules have a MW of typically more than 1,000, in most cases more than 10,000, up to 500,000 and more. Macromolecules comprise on the one hand the above biomolecules. On the other hand, the macromolecules also include organic polymeric compounds, which are not built up from natural molecular components or modified such components. Such polymeric compounds are polymerization products from organic monomers, identical or different, for instance plastic materials.

The term macromolecule species or biomolecule species designates a defined molecular structure. Macromolecules or biomolecules of a species comprise "identical" molecular structures, the term "identical" comprising at least 80%, preferably at least 90%, usually more than 95% up to 100% agreement, in reference to the chemical formula or the sequence.

The fluorescence emitter contains for instance an aromatic molecular structure, such as a benzene ring or a corresponding hetero ring. In proteins, benzene rings exist for instance in tryptophan, tyrosine and phenylalanine. An aromatic hetero ring exists further for instance in adenine. Moreover, fluorescent molecules accumulating at or reacting with macromolecules, for instance rhodamine or dextran blue, may be added, thus the macromolecules or biomolecules being provided with a fluorescence emitter.

A solution volume may typically be in the range from 0.001 μl to 10 ml, in particular 0.01 μl to 0.1 ml. In the case of high-throughput experiments, a solution volume is usually in the range from 0.01 μl to 100 μl, in particular 0.01 μl to 5 μl.

Visible light has wavelengths between approx. 380 nm and 800 nm. UV light has wavelengths between less than 380 nm and approx. 1 nm. IR light has wavelengths between more than 800 nm and 10,000 nm, in the case of the near IR between more than 800 nm and 2,000 nm.

Crystallization conditions are achieved by adding substances to a solution having macromolecules and/or subjecting the solution to physical or physical-chemical conditions (temperature, pressure, concentration, salt concentration, etc.), which will lead to a crystallization of the macromolecules or prospectively lead thereto.

In the context of the invention, the term solution also comprises gels.

Suitable crystal sizes for x-ray structure analysis for example, are typically in the range of 0.001 to 50 μl, in particular 0.01 to 5 μl. The required particle size is usually at least 10% of the above minimum value, preferably within the specified range.

In the following, the invention is explained in more detail with reference to embodiments representing examples of execution only.

1: EXEMPLARY APPARATUS STRUCTURE ACCORDING TO THE INVENTION

In FIG. 1 is shown the apparatus according to the invention. It shows a carrier element 7 comprising a multitude of depressions 8. The carrier element 7 is transparent for visible light. In the depressions 8 is applied one solution volume each containing biomolecules of a biomolecule species, beside the solvent. In the example, the biomolecule species is glucose isomerase. With regard to the other components, reference is made to example 2.

Above the carrier element 7 can be seen the essential elements of a DLS apparatus, namely a measuring head 10, in which the ends of two light conductors 11, 12 are arranged and fixed. To the opposite end of the light conductor 12, a laser 13 is optically connected. The monochromatic light emitted by the laser 13 is directed by means of the light conductor 12 onto the solution volume (measurement position) centrally disposed in FIG. 1. To the opposite end of the light conductor 11, a fast and sensitive detector 14, for instance a photomultiplier, is optically connected. Photons back-scattered from the solution volume enter into the light conductor 11, pass therethrough to the detector 14 and are thus measured. An evaluation unit 15 connected to the detector 14 detects the time fluctuations of the back-scattered intensity at the wavelength of the laser 13, thereby at last signals or data correlated with a particle size or particle size distribution being obtained. For the arrangement of the ends of the light conductors 11, 12, the configuration is thus that the spatial angles of the light emission and of the detection of back-scattered photons are focused in the solution volume. Due to the low particle density or biomolecule crystals density and the low requirements with regard to the measuring accuracy, it is not necessary to detect in different back-scattering angles or to use different primary light wavelengths.

Above the carrier element 7, further, a camera 1 with a lens 2 and a UV filter 3 are provided. The UV filter is opaque to UV, however transparent for the longer wavelengths of the fluorescence light. For the fluorescence excitation, a UV light source 5 emitting at approx. 360 nm is provided, the light of which is conducted through a semi-transparent mirror into that solution volume, into which the monochromatic light emitted by the laser 13 is focused. By means of the camera 1, a two-dimensional picture of the solution volume or of a part thereof is recorded. The camera is connected to an electronic evaluation circuitry detecting the maximum intensities of light dots or light dot clusters on the sensor of the camera.

Finally can be seen a light source 4 for visible light, which is disposed underneath the transparent carrier element 7, and which emits the light in the direction of the camera through the carrier element 7. Since the mirror is semi-transparent, a normal transmitted light picture of the solution volume can thus be obtained and observed by the camera 1.

The carrier element 7 is arranged on a base element 6, which is adapted as a movable table. The base element 6 is movable back and forth by means of a control device and drive elements mechanically connected to the base element in directions parallel to the main faces of the carrier element 7 or of the base element 6. The control device causes different solution volumes to be moved subsequently according to step-on signals into the measurement position, which is characterized by that the solution volume to be measured comes to rest in the focus of the DLS apparatus.

2: CRYSTALLIZATION OF A BIOMOLECULE

In the solution volumes of the carrier element 7, the following crystallization tests are performed, by determining the optimum precipitation concentration of ammonium sulfate for the precipitation of glucose isomerase.

As carrier element 7, a Linbro plate is used. Into two chambers each of the Linbro plate, 500 μl identical ammonium sulfate solutions (buffer) from a concentration series, beginning at 1.5 M, ending at 2.6 M, increasing in 0.1 M steps, are brought. A set of solution volume pairs of the respective concentration stages is obtained. The borders of the solution volumes are respectively provided with a rim of a silicon mass for sealing purposes.

In parallel, a set of siliconed cover slips is provided with 3 μl protein solution (30 mg/ml buffer) and 3 μl ammonium sulfate solution by central application. Then cautious mixing is performed. One pair of cover slips each corresponds with the solution volume pairs because of the respectively identical ammonium sulfate concentrations. The cover slips are turned upside down and pressed on the solution volumes in the Linbro plate or on the rims, and the above assignment because of the ammonium sulfate concentrations is observed.

After setting-down all cover slips, the cover of the Linbro plate is slightly raised by means of a modeling clay and placed on the Linbro plate. Finally, an assignment and registration of the respective ammonium sulfate concentrations with respect to the positions of the solution volumes are performed. Then the crystallization experiment is executed at 4° C. for 12 h in a refrigerator.

3: HIGH-THROUGHPUT CRYSTALLIZATION EXPERIMENTS USING THE METHOD ACCORDING TO THE INVENTION

After terminating the crystallization experiment of example 2, the carrier element 7 of example 2 is taken from the refrigerator and placed in the apparatus according to example 1. The control device of the base element 6 is initialized, which moves a first solution volume into the measurement position.

Then the DLS apparatus is activated by an enabling signal of the control device, and the measurement of back-scattered light or of the intensity fluctuations thereof is started. The measured value obtained after termination of the measurement and correlated with a particle size or particle size distribution is compared in the evaluation unit 15 to the corresponding minimum measured value, and if this comparison indicates the presence of particles of a defined minimum size, a first positive signal is generated. Otherwise, a negative signal is generated.

Thereupon, the UV light source 5 and the camera 1 are activated by the evaluation unit 15, and a fluorescence picture is recorded. The evaluation unit 15 then compares the measured intensities of the picture dots or picture dot clusters of the fluorescence picture to a minimum intensity value, which is above the intensity of the fluorescence of the solution volume with protein, however without crystallization (background). According to this comparison in the evaluation unit 15, a second positive or negative signal is generated.

The first and second positive or negative signals are then assigned in the evaluation unit 15 to the solution volume in the measurement position and are stored. If for a certain solution volume a first as well as a second positive signal is recorded, this will indicate that in the respective solution volume a protein crystallization (and not a salt crystallization) has taken place.

After the first and second signals have been obtained for the first solution volume, the evaluation unit 15 generates the step-on signal causing the next solution volume to be moved into the measurement position, by the movement of the base element 6. Thereafter another step-on signal is generated causing the process as described above for the first solution volume to be activated for the second solution volume now. This is repeated for each solution volume, until there have been obtained and assigned first and second positive or negative signals for each solution volume.

During the measurements or after termination of all measurements, the evaluation unit 15 may produce on a display a representation of the carrier element with the solution volumes, which can be shown in different colors as per the assigned first and second positive or negative signals. Solution volumes with assigned first and second positive signals may for instance appear in red for indicating a successful crystallization test. Solution volumes with first positive signal and second negative signal may for instance appear in blue for indicating a salt crystallization without protein crystallization. Solution volumes with first and second negative signals may for instance appear in white for indicating the absence of any crystallization at all.

In lieu of a display or in addition thereto, the first and second positive or negative signals may be used for controlling further automatic processes, for instance the preparation of solution volumes selected according to first and second positive signals for the x-ray structure analysis.

Overall, a multitude of crystallization experiments and subsequent structure analysis can be performed automatically with comparatively very high speed and reliability.

The invention claimed is:

1. A method for monitoring the production of macromolecule crystals containing at least one fluorescence emitter, comprising the following steps:

a) a solution volume with dissolved macromolecules of a molecule species containing at least one fluorescence emitter is subjected to conditions which cause the macromolecules to crystallize to macromolecule crystals or which are expected to cause the macromolecules to crystallize to macromolecule crystals, b) the solution volume of step a) is irradiated with coherent light, and the light scattered by the macromolecule crystals is detected in at least one defined spatial angle range by means for the detection of scattered light, c) before, simultaneously with or after step b), the solution volume is irradiated with a light source, the light emission of which is suitable for exciting the fluorescence emitter, and the fluorescence light is detected by means for the detection of fluorescence light.

2. A method according to claim 1, wherein the macromolecule species is a biomolecule species.

3. A method according to claim 1, wherein the following steps are added:

d) the signals produced by the means for the detection of scattered light are fed to an evaluation unit, in which the signals are transformed into a particle size or a measurement value correlated herewith, the particle size or the measurement value being compared to a defined required particle size or required measurement value, e) the signals produced by the means for the detection of fluorescence light are fed to an evaluation unit, in which the signals are transformed into a fluorescence intensity, and the fluorescence intensity is compared to a required fluorescence intensity, f) macromolecule crystals are selected, if the particle size is larger than the required particle size and simultaneously the fluorescence intensity is larger than the required fluorescence intensity.

4. A method according to claim 3, wherein a multitude of solution volumes comprising identical or different macromolecule species are subjected simultaneously or subsequently to the steps a) to c) or a) to f), and the crystallization conditions of step a) can be identical or different in the various solution volumes.

5. A method according to claim 4, wherein the multitude of solution volumes are arranged on or in a carrier element.

6. A method according to claim 4 or 5, wherein the number of solution volumes is in the range 5 to 1,000.

7. A method according to claim 1, wherein the steps b) and c) are performed one after the other, b) after c) or c) after b).

8. A method according to claim 1, wherein the light source used in step c) is a UV light source.

9. A method according to claim 1, wherein the means for the detection of scattered light or the means for the detection of fluorescence light comprise a light conductor connected thereto with one of its ends, and the opposite end thereof is directed onto the solution volume.

10. A method according to claim 1, wherein the means for the detection of the scattered light or of the fluorescence light comprise a photomultiplier.

11. A method according to claim 1, wherein a UV filter is interposed between the solution volume and the means for the detection of fluorescence light.

12. A device for monitoring, preferably high-throughput monitoring, the production of macromolecule crystals, comprising:

a carrier element disposed on a base element, and onto or into said carrier element a solution volume containing dissolved macromolecules of a macromolecule species can be applied, at least one light source for coherent light to be directed onto the solution volume, a light source for light, which is suitable for the excitation of a fluorescence emitter, to be directed onto the solution volume, means for the detection of scattered light from the solution volume, means for the detection of fluorescence light from the solution volume, and an evaluation unit connected to the means for the detection of scattered light and the means for the detection of fluorescence light.

13. A device according to claim 12, wherein the carrier element comprises a multitude of sample areas for receiving one solution volume each.

14. A device according to claim 12, wherein the means for the detection of scattered light or the means for the detection of fluorescence light either comprise a common light conductor or a respectively assigned light conductor, the free end of which is directed onto the solution volume.

15. A device according to claim 14, wherein the free end of the light conductor is arranged for receiving light, which is emitted from the solution volume in an angle of 0° to 70° with respect to the axis of the irradiated light.

16. A device according to claim 12, wherein either the carrier element or the means for the detection of scattered light and the means for the detection of fluorescence light are displaceable relative to the base element by means of a manipulator device.

17. A method according to claim 4 or 5, wherein the number of solution volumes is in the range of 50 to 500.

18. A method according to claim 3, wherein the steps b) and c) are performed one after the other, b) after c) or c) after b).

19. A method according to claim 3, wherein the means for the detection of scattered light or the means for the detection of fluorescence light comprise a light conductor connected thereto with one of its ends, and the opposite end thereof is directed onto the solution volume.

20. A method according to claim 3, wherein a UV filter is interposed between the solution volume and the means for the detection of fluorescence light.

* * * * *